United States Patent
Danhier et al.

(10) Patent No.: US 12,383,520 B2
(45) Date of Patent: Aug. 12, 2025

(54) COMPOUND AND COMPOSITION FOR USE IN THE TREATMENT OF PREMENSTRUAL SYNDROME AND/OR PREMENSTRUAL DYSPHORIC DISORDER

(71) Applicant: SYNAPHARM INDUSTRIAL SYNTHESIS, Alleur (BE)

(72) Inventors: Philippe Danhier, Audregnies (BE); Pascale Azzam, Alleur (BE)

(73) Assignee: SYNAPHARM INDUSTRIAL SYNTHESIS, Alleur (BE)

( * ) Notice: Subject to any disclaimer, the term of this patent is extended or adjusted under 35 U.S.C. 154(b) by 773 days.

(21) Appl. No.: 17/610,366

(22) PCT Filed: May 12, 2020

(86) PCT No.: PCT/EP2020/063120
§ 371 (c)(1),
(2) Date: Nov. 10, 2021

(87) PCT Pub. No.: WO2020/229443
PCT Pub. Date: Nov. 19, 2020

(65) Prior Publication Data
US 2022/0218633 A1 Jul. 14, 2022

(30) Foreign Application Priority Data

May 16, 2019 (BE) .................................. 2019/5324
May 16, 2019 (EP) .................................. 19174909

(51) Int. Cl.
*A61K 31/185* (2006.01)
*A61K 33/06* (2006.01)

(52) U.S. Cl.
CPC ............ *A61K 31/185* (2013.01); *A61K 33/06* (2013.01)

(58) Field of Classification Search
CPC .............................. A61K 31/185; A61K 33/06
See application file for complete search history.

(56) References Cited

U.S. PATENT DOCUMENTS

| | | | | |
|---|---|---|---|---|
| 2010/0074960 A1* | 3/2010 | Brandon | .............. | A61K 9/2027 424/490 |
| 2015/0132275 A1 | 5/2015 | Suovaniemi | | |
| 2016/0367596 A1 | 12/2016 | Profet | | |
| 2018/0036340 A1 | 2/2018 | Profet | | |
| 2020/0237812 A1 | 7/2020 | Danhier | | |

FOREIGN PATENT DOCUMENTS

| | | | | |
|---|---|---|---|---|
| BE | 1025644 A1 | 5/2019 | | |
| CN | 1293573 A | 5/2001 | | |
| CN | 104427983 A | 3/2015 | | |
| EP | 1661575 | * | 5/2006 | |
| EP | 1661575 A1 | * | 5/2006 | ........... A61K 9/2077 |
| FR | 2878160 | * | 5/2006 | |
| KR | 10-2016-0008257 A | 1/2016 | | |
| WO | 2016/205089 A1 | 12/2016 | | |

OTHER PUBLICATIONS

Briden (2018).*
Rafi et al. (Current Psycharity 16(9), 2008).*
Guerrera et al. (American Family Physician 80(2), 2009).*
Uysal et al. (Bio trace Elem Res (2019) with Epub Apr. 21, 2018)).*
Facchinetti: "Oral magnesium successfully relieves premenstrual mood changes" Obstet Gynecol., vol. 78, No. 2, Aug. 1, 1991 (Aug. 1, 1991), pp. 177-181, XP055642344.
Quaranta S et al.: "Pilot study of the efficacy and safety of a modified-release magnesium 250mgtablet (Sincromag((R))) for the treatment of premenstrual syndrome" Clinical Drug Investigation, ADIS International, Auckland, NZ, vol. 27, No. 1, Jan. 1, 2007 (Jan. 1, 2007), pp. 51-58, ISSN: 1173-2563, XP009092161.
Nazan et al.: "Timeline (Bioavailability) of Magnesium Compounds in Hours: Which Magnesium Compound Works Best?", vol. 187, No. 1, Apr. 21, 2018 (Apr. 21, 2018), pp. 128-136, Biological Trace Element Research, Humana Press, Clifton, NJ, US, ISSN: 0163-4984, XP036665312.
Kharitonova et al.: "Comparative angioprotective effects of magnesium compounds" Journal of Trace Elements in Medicine and Biology, US, vol. 29, Jan. 1, 2015 (Jan. 1, 2015), pp. 227-234 ISSN: 0946-672X, XP055642261.
Durlach: "Mg Acetyltaurinate as a photic inhibitor in photosensitive magnesium depletion: a physiological pathway in headache with photophobia treatment" Jan. 1, 2013 (Jan. 1, 2013), XP055485521.
International Search Report issued by the International Searching Authority in corresponding International Application No. PCT/EP2020/063120 on Jul. 23, 2020, 12 pages.
Arfuzir et al., "Protective Effect of Magnesium Acetyltaurate Against Endothelin-Induced Retinal and Optic Nerve Injury," Neuroscience, Elsevier Ltd., published Mar. 25, 2016, 12 pages.
China National Intellectual Property Administration, "First Office Action and Search Report," issued in connection with Chinese Patent Application No. 202080036395.4, dated Sep. 2, 2022, 12 pages. [English Machine Translation Included].
China National Intellectual Property Administration, "Second Office Action and Supplementary Search Report," issued in connection with Chinese Patent Application No. 202080036395.4, dated Feb. 28, 2023, 13 pages. [English Translation Included].
China National Intellectual Property Administration, "Third Office Action and Supplementary Search Report," issued in connection with Chinese Patent Application No. 202080036395.4, dated Jul. 11, 2023, 13 pages. [English Translation Included].
European Patent Office, "Decision to Grant", issued in connection with European Application No. 19174909.2, dated Feb. 17, 2022, 2 pages.

(Continued)

*Primary Examiner* — Shirley V Gembeh
(74) *Attorney, Agent, or Firm* — HANLEY, FLIGHT & ZIMMERMAN, LLC

(57) ABSTRACT

This invention pertains to a compound and a composition for use in the treatment of premenstrual syndrome and/or premenstrual dysphoric disorder.

18 Claims, No Drawings

(56) References Cited

OTHER PUBLICATIONS

European Patent Office, "Intention to Grant", issued in connection with European Application No. 19174909.2, dated Oct. 27, 2021, 5 pages.
European Patent Office, "Search Report", issued in connection with European Application No. 19174909.2, dated Nov. 18, 2019, 10 pages.
Thwin et al., "Fluctuations in Serum magnesium and Systemic Arterial Blood Pressures during the Menstrual Cycle in young reproductive women," Research J. Pharm. and Tech., 15(2): Feb. 8, 2022, 1 page.
Thys-Jacobs, "Micronutrients and the premenstrual syndrome: the case for calcium," J Am Coll Nutr, 19(2), Apr. 2000, 1 page.

\* cited by examiner

COMPOUND AND COMPOSITION FOR USE IN THE TREATMENT OF PREMENSTRUAL SYNDROME AND/OR PREMENSTRUAL DYSPHORIC DISORDER

This patent arises from the U.S. national stage of International Patent Application Serial No. PCT/EP2020/063120, having an international filing date of May 12, 2020, and claims benefit of Belgian Patent Application No. BE2019/5324, filed on May 16, 2019 and European Patent Application No. 19174909.2. filed on May 16, 2019, which are hereby incorporated by reference in their entireties for all purposes.

This invention pertains to a compound and a composition for use in the treatment of premenstrual syndrome and/or premenstrual dysphoric disorder.

Premenstrual syndrome (or PMS) is a group of disorders occurring during the days before or during menstruation. It is characterised by various symptoms such as painful swelling of breasts, headaches, heavy legs or weight gain, skin rashes or herpes and by behavioural or mood disturbances including nervousness. anxiety, aggressiveness, emotionality, depression. Premenstrual dysphoric disorder (PMDD) is recognised as the most severe form of the premenstrual syndrome.

A general review of the literature (Zaafrane et al., Journal de Gynécologie Obstétrique et Biologie de la Reproduction, 36, 2007, 642-652) defines premenstrual syndrome as a set of somatic, affective and behavioural symptoms appearing before the period and disappearing after the period is over. This review states that this symptomatic set can affect approximately 75% women of childbearing age and that, presently, the treatments of premenstrual symptomatology are varied, have indications that are not very clear and effectiveness that is not well established.

According to the same general review of the literature, premenstrual syndrome can combine more than a hundred somatic, cognitive, behavioural or affective symptoms. However, the most frequent complaints come in the form of a characteristic triad:
 a) breast tension: breasts are tender, sensitive, hypervascularised, painful, may interfere with the arm movements;
 b) abdominopelvic tension: more or less pronounced abdominal bloating, always uncomfortable, often associated with constipation, or pelvic heaviness with a discomfort when wearing clothes and occasional premenstrual weight gain;
 c) mental tension: the most frequent neuropsychological disorders are irritability, mood lability, depression, anxiety, asthenia, sleep and eating disorders and headaches.

The objective of the treatment in PMS is a reduction in symptoms and an improvement in the general condition. There are drug treatments that are essentially based on taking antidepressants and/or anxiolytics and/or contraceptives and/or progesterone and/or GnRH agonists. The molecules used include triptans (for example Sumatriptan or Rizatriptan) as well as ergot derivatives that unfortunately have many side effects: alteration in taste; dry mouth; hot flashes; muscle soreness; shortness of breath; dizziness; fatigue; nausea or vomiting; heaviness; numbness; headache; weakness and drowsiness.

There are alternative therapies as well and are mainly represented by dietary supplements including vitamin B6 and/or magnesium (up to 200 to 400 mg/day) and/or manganese and/or vitamin E. There also are food supplements with their main ingredient being evening primrose or borage oil, vitamin B and magnesium.

Magnesium has been identified quite quickly as an important element in the treatment of PMS. In fact, it is recognised that a magnesium deficiency is common in nearly all the forms of premenstrual syndrome and that an intake of this mineral is favourable to its treatment. This is why compositions proposed for the treatment of PMS and comprising magnesium, particularly magnesium in the form of salts, are known. In fact, today, there are various magnesium salts used in the treatment of PMS, such as e.g. magnesium oxide or magnesium threonate. In this sense, the EP1661575 document discloses compositions comprising a mixture of magnesium oxide and magnesium stearate.

Unfortunately, at present, it appears that the main drug treatments give rise to numerous side effects and that the alternative treatments are relatively less effective and are therefore not used much.

There is thus, till today, no drug treatment without side effects and alternative treatments are not convincing. There is thus a real need to develop and formulate an alternative compound and/or composition that is effective, safe and minimises or even eliminates, at least partially, the side effects such as those listed above to ensure an appropriate and optimised treatment for premenstrual syndrome and/or premenstrual dysphoric disorder.

To solve this problem, this invention provides a compound and a composition for use in the treatment of premenstrual syndrome and/or premenstrual dysphoric disorder, the said compound being magnesium N-acetyl-taurinate and the said composition comprising magnesium N-acetyl-taurinate.

In the context of this invention, it has been determined that the compound according to the invention, i.e. magnesium N-acetyl-taurinate, is more effective (reduction of symptoms) than the other compounds, particularly more effective than the other magnesium salts known from the state of the art (like magnesium oxide) for their use in the treatment of premenstrual syndrome and/or premenstrual dysphoric disorder. In addition, a composition according to the invention involves an acceptable cost and is both effective and safe for the treatment of premenstrual syndrome and/or premenstrual dysphoric disorder.

Note that magnesium N-acetyl-taurinate ($C_8H_{16}MgN_2O_8S_2$) is known for its protective cyto-vasculo properties such as the protective and platelet antiaggregates of arterial and venous thromboses as well as a stabilising action of the red corpuscle membrane. In addition, magnesium Nacetyl-taurinate has been shown to protect against glaucoma by acting on vascular deregulation, as well as to have angio-protective properties of magnesium N-acetyl-taurinate by its anti-inflammatory action by restoring the levels of eNOS (endothelial Nitric Oxide Synthase 3). Studies have also shown magnesium Nacetyl-taurinate to have a beneficial effect on neurotoxicity due to hyperexcitability of ionotropic glutamatergic receptors. In fact, magnesium N-acetyl-taurinate has an intraneuronal action not only on the NMDA receptor but also on the two other ionotropic receptors for glutamic acid, i.e. the AMPA and KA receptors, both involved in the speed of synaptic transmission. It has been observed that such a compound has a structural analogy with glutamic acid as well as kainic acid. Thus, magnesium N-acetyl-taurinate will target all the glutamatergic receptors NMDAR, AMPAR and KAR, thus causing the inhibition of the signaling pathways downstream of these receptors.

Advantageously, according to the invention, the magnesium N acetyl-taurinate is magnesium N-acetyl-taurinate dihydrate comprising two intrinsic water molecules.

In the context of this invention, the terms "two intrinsic water molecules" mean that the two water molecules are inherent to the magnesium N-acetyl-taurinate dihydrate, i.e. that 'they are an integral part of the magnesium N-acetyl-taurinate dihydrate, unlike hydration water that could be absorbed or adsorbed by this compound.

Magnesium N-acetyl-taurinate dihydrate ($C_8H_{20}MgN_2O_{10}S_2$) is a magnesium vector and magnesium analogue of taurine that has a molecular weight of 392.677 g/mol, two water molecules ($H_2O$) being intrinsic to the magnesium N-acetyl-taurinate dihydrate molecule.

Particularly speaking, magnesium N-acetyl-taurinate dihydrate is what is produced and marketed under the ATAMg® trademark by the company Synapharm Industrial Synthesis.

Like the non-dihydrate magnesium N-acetyl-taurinate, magnesium N-acetyl-taurinate dihydrate comprising two intrinsic water molecules has different characteristics such as a sulphated amino-3 derivative, a sulphonic (non-carboxylic) acid, an N-acetylate, does not have the amphoteric nature of taurine (Zwitterion form, i.e. a positive charge and a negative charge present on the same residue) and optimises the intracellular taurinergic nature. As the electrical charge on the nitrogen of taurine is removed by acetylation, only the electrons of the $Mg^{++}$ cation are kept chelated by the two sulfonic radicals of taurine. This leads to an ethanamide (acetamide) derivative that has a more marked lipophilic nature than that of amphoteric taurine, which facilitates penetration through the neuronal membrane phospholipids. Ethanamide (acetamide) derivatives characterise the molecules used for their nootropic (like piracetam), anti-convulsant and anti-epileptic (like levitracetam) actions.

The molecular weight of magnesium N-acetyl-taurinate dihydrate is 392.677 g/mol and differs from that of non-dihydrate magnesium N-acetyl-taurinate ($C_8H_{16}MgN_2O_8S_2$) that is 356.656 g/mol. This form, which is not dihydrated, is mainly described in the FR2384751 document where magnesium N-acetyl-taurinate is obtained by mixing magnesia, taurine, water and acetic acid before two successive drying steps, one under vacuum at 100° C. and the other with a drying solvent, so as to obtain crystals.

Moreover, it has been determined that magnesium N-acetyl-taurinate in dihydrate form comprising two intrinsic water molecules shows stability over time which is increased as compared to non-dihydrate magnesium N-acetyl-taurinate, i.e. compared to anhydrous magnesium N-acetyl-taurinate. In other words, it has been shown that the dihydrate form of magnesium N-acetyl taurinate best maintains its properties over time in comparison with the anhydrous form of magnesium N-acetyl-taurinate.

It was also determined that the two intrinsic water molecules are responsible for the formation of a stable complex by establishing bonds between the two intrinsic water molecules and the magnesium present in the magnesium N-acetyl-taurinate dihydrate compound. More particularly, magnesium bonds with the Nacetyl-taurine and water through non-covalent bonds of the metal ligand coordination bonds type.

Furthermore, as indicated above, the compound according to the invention is safe and beneficial (beyond its properties stated above) for the human body. In fact, magnesium contributes to maintaining the balance of fluids and electrolytes, normal protein synthesis and energy metabolism, suitable muscle functions, reduction in fatigue and asthenia, maintaining good dentition and an appropriate bony structure and contributes to the normal functioning of the nervous system and the psychological function.

In addition, N-acetyl-taurinate helps the cellular penetration of magnesium and taurine and acts on the maintenance of cellular osmolarity.

Preferably, the compound is in an orally administrable form, for example in the form of a tablet, pill, capsule, medication, soluble powder, oily solution, an effervescent tablet or soft capsule.

In a particular form according to the invention, the compound is administered at a rate of 2 to 3 capsules per day.

Other embodiments of the compound according to the invention are indicated in the appended claims.

This invention also pertains to a composition for use in the treatment of premenstrual syndrome and/or premenstrual dysphoric disorder.

Advantageously, in a composition according to the invention, the said magnesium N-acetyl-taurinate is magnesium N-acetyl-taurinate dihydrate comprising two intrinsic water molecules.

In the context of this invention, the terms "two intrinsic water molecules" mean that the two water molecules are inherent to the magnesium N-acetyl-taurinate dihydrate, i.e. that 'they are an integral part of the magnesium N-acetyl-taurinate dihydrate, unlike hydration water that could be absorbed or adsorbed by this compound.

Magnesium N-acetyl-taurinate dihydrate ($C_8H_{20}MgN_2O_{10}S_2$) is a magnesium vector and magnesium analogue of taurine that has a molecular weight of 392.677 g/mol, two water molecules ($H_2O$) being intrinsic to the magnesium N-acetyl-taurinate dihydrate molecule.

Particularly speaking, magnesium N-acetyl-taurinate dihydrate is what is produced and marketed under the ATAMg® trademark by the company Synapharm Industrial Synthesis.

The molecular weight of magnesium N-acetyl-taurinate dihydrate is 392.677 g/mol and differs from that of non-dihydrate magnesium N-acetyl-taurinate ($C_8H_{16}MgN_2O_8S_2$) that is 356.656 g/mol. This form, which is not dihydrated, is mainly described in the FR2384751 document where magnesium N-acetyl-taurinate is obtained by mixing magnesia, taurine, water and acetic acid before two successive drying steps, one under vacuum at 100° C. and the other with a drying solvent, so as to obtain crystals.

It was also determined that the two intrinsic water molecules are responsible for the formation of a stable complex by establishing bonds between the two intrinsic water molecules and the magnesium present in the magnesium N-acetyl-taurinate dihydrate compound. More particularly, magnesium bonds with the Nacetyl-taurine and water through non-covalent bonds of the metal ligand coordination bonds type.

The formation of such a complex is particularly advantageous as the latter ensures increased stability of the compound: the magnesium remains fixed (trapped) to the complex.

Advantageously, the magnesium N-acetyl-taurinate or the magnesium N-acetyl-taurinate dihydrate comprising two intrinsic water molecules is present up to 40 to 60% by weight with respect to the total weight of the composition.

In a particularly advantageous form, the composition according to the invention also includes taurine up to 10 to 15% by weight with respect to the total weight of the composition.

Advantageously, the composition according to the invention also comprises at least an additional magnesium compound selected in the group comprising magnesium salts of amino acids, magnesium citrate, magnesium gluconate, magnesium lactate, magnesium malate, magnesium taurate, magnesium bisglycinate, magnesium glycerophosphate, magnesium threonate, magnesium pidolate, their derivatives and mixtures.

Preferably, according to the invention, the composition also includes magnesium up to 8 to 15% by weight with respect to the total weight of the composition.

In addition, in a particular embodiment, the composition also comprises at least one amino acid, for example threonine.

Preferably, the said at least one amino acid is glycine present up to 10 to 15% by weight with respect to the total weight of the composition.

Advantageously, the said at least one amino acid is threonine present up to 10 to 15% by weight with respect to the total weight of the composition.

In a particular form, according to the invention, the composition also comprises at least one vitamin selected in the group consisting of vitamin B1, B2, B6 and their mixtures.

Advantageously, according to the invention, the said at least one vitamin is vitamin B1 present up to 0.05 to 0.1% by weight with respect to the total weight of the composition.

Preferably, the said at least one vitamin is vitamin B2 present up to 0.05 to 0.1% by weight with respect to the total weight of the composition.

In a particularly advantageous embodiment, according to the invention, the said at least one vitamin is vitamin B6 present up to 0.05 to 0.15% by weight with respect to the total weight of the composition.

Advantageously, the composition also comprises at least one pharmaceutically acceptable excipient, preferably four pharmaceutically acceptable excipients, selected in the group comprising glyceryl behenate, sucrose stearate, microcrystalline cellulose, magnesium stearate, silicon dioxide, pea maltodextrin and their mixtures.

In a particular form, the composition according to the invention is in the form of a medicine.

Preferably, the composition according to the invention is in the form of a food supplement.

Advantageously, the composition according to the invention is in the form of a drink.

In a particularly advantageous embodiment according to the invention, the composition is in an orally administrable form, for example in the form of a tablet, pill, capsule, medication, soluble powder, oily solution, an effervescent tablet or soft capsule.

Moreover, in a particular embodiment, the composition according to the invention is administered at a rate of 2 to 3 capsules per day.

Other embodiments of the composition according to the invention are indicated in the appended claims.

This invention has been described in relation to specific embodiments, which have a purely illustrative value and should not be considered as limiting. Generally, it will be obvious to those skilled in the art that this invention is not limited to the examples illustrated and/or described above.

The use of the verbs "comprise", "include", "consist of", or any other variant, as well as their conjugations, can in no way exclude the presence of elements other than those mentioned herein.

The use of the indefinite article "a", "an", or the definite article "the", to introduce an element does not exclude the presence of a plurality of these elements.

The invention claimed is:

1. A method of treating premenstrual syndrome and/or premenstrual dysphoric disorder, the method comprising administrating to a subject magnesium N-acetyl-taurinate.

2. The method according to claim 1, wherein the subject is a subject suffering from or diagnosed with premenstrual syndrome and/or premenstrual dysphoric disorder.

3. The method according to claim 1, wherein the magnesium N-acetyl-taurinate is magnesium N-acetyl-taurinate dihydrate comprising two intrinsic water molecules.

4. The method of claim 1, wherein the magnesium N-acetyl-taurinate is included in a composition that also includes an additional magnesium compound selected in the group comprising magnesium salts of amino acids, magnesium citrate, magnesium gluconate, magnesium lactate, magnesium malate, magnesium taurate, magnesium bisglycinate, magnesium glycerophosphate, magnesium threonate, magnesium pidolate, their derivatives and mixtures.

5. The method of claim 1, wherein the magnesium N-acetyl-taurinate is included in a composition that also includes four pharmaceutically acceptable excipients selected in the group comprising glyceryl behenate, sucrose stearate, microcrystalline cellulose, magnesium stearate, silicon dioxide, pea maltodextrin, and their mixtures.

6. The method of claim 1, further including causing effects across multiple body systems in the subject with the magnesium N-acetyl-taurinate.

7. The method of claim 1, further including causing somatic effects with the magnesium N-acetyl-taurinate and causing cognitive effects with the magnesium N-acetyl-taurinate.

8. The method of claim 7, further including causing behavioral effects with the magnesium N-acetyl-taurinate.

9. The method of claim 1, wherein the magnesium N-acetyl-taurinate is included in a composition and forms about 40% to about 60% of the total weight of the composition.

10. The method of claim 9, wherein the composition includes an amino acid that forms about 10% to about 15% of the total weight of the composition.

11. The method of claim 9, wherein the composition includes vitamin B1 that forms about 0.05% to about 0.1% of the total weight of the composition.

12. The method of claim 9, wherein the composition includes vitamin B2 that forms about 0.05% to about 0.1% of the total weight of the composition.

13. The method of claim 9, wherein the composition includes vitamin B6 that forms about 0.05% to about 0.15% of the total weight of the composition.

14. The method of claim 9, wherein the composition includes taurine that forms about 10% to about 15% of the total weight of the composition.

15. The method of claim 1, wherein the magnesium N-acetyl-taurinate is included in a composition that includes 59.2% by weight of magnesium N-acetyl-taurinate, 4.6% by weight of a first excipient, 34.6% by weight of a second excipient different than the first excipient, and 1.5% by weight of a fatty acid.

16. The method of claim 1, wherein the magnesium N-acetyl-taurinate is included in a composition that includes about 60% by weight of magnesium N-acetyl-taurinate and about 40% by weight of at least two excipients.

17. A method of treating both a somatic premenstrual syndrome and a cognitive premenstrual syndrome, the method comprising administrating to a subject magnesium N-acetyl-taurinate.

18. A method of treating premenstrual syndrome and/or premenstrual dysphoric disorder, the method comprising administrating to a subject magnesium N-acetyl-taurinate, wherein administration of the magnesium N-acetyl-taurinate causes treatment effects to multiple premenstrual syndrome symptoms across multiple body systems of the subject.

* * * * *